United States Patent
Waldenburg

[11] Patent Number: 5,840,584
[45] Date of Patent: Nov. 24, 1998

[54] BLOOD IN FECES TEST DEVICE

[76] Inventor: Ottfried Waldenburg, P. O. Box 548, Sells, Ariz. 85634

[21] Appl. No.: 481,651

[22] Filed: Jun. 7, 1995

[51] Int. Cl.⁶ .................................................. G01N 33/72
[52] U.S. Cl. ........................ 436/66; 436/165; 436/169; 436/170; 422/55; 422/56; 422/58; 422/69; 435/287.6; 435/287.7; 435/287.8; 600/371; 600/572; 604/318
[58] Field of Search .............................. 436/66, 164, 165, 436/169, 170; 422/55, 56, 58, 69; 435/287.6, 287.7, 287.8; 128/759, 638; 604/318; 600/362, 371, 562, 572

[56] References Cited

U.S. PATENT DOCUMENTS

| | | | |
|---|---|---|---|
| 3,672,351 | 6/1972 | Ubersax et al. | 600/371 |
| 3,996,006 | 12/1976 | Pagano | 422/50 |
| 4,273,741 | 6/1981 | Levine | 422/56 |
| 4,473,079 | 9/1984 | Jasper et al. | 600/371 |
| 4,511,533 | 4/1985 | Guadagno et al. | 422/61 |
| 4,541,987 | 9/1985 | Guadagno | 422/56 |
| 4,559,949 | 12/1985 | Levine | 600/371 |
| 4,562,043 | 12/1985 | Mennen et al. | 422/56 |
| 4,578,358 | 3/1986 | Oksman et al. | 436/66 |
| 4,582,685 | 4/1986 | Guadagno et al. | 422/61 |
| 4,645,743 | 2/1987 | Baker et al. | 436/66 |
| 4,647,541 | 3/1987 | Guadagno et al. | 436/66 |
| 4,675,160 | 6/1987 | Talmage et al. | 422/56 |
| 4,725,553 | 2/1988 | Guadagno | 436/66 |
| 4,804,518 | 2/1989 | Levine et al. | 422/56 |
| 4,808,379 | 2/1989 | Wardlaw et al. | 422/56 |
| 4,956,300 | 9/1990 | Wells | 436/66 |
| 5,064,766 | 11/1991 | Wardlaw et al. | 436/66 |
| 5,171,528 | 12/1992 | Wardlaw | 422/56 |
| 5,171,529 | 12/1992 | Schreiber | 422/58 |
| 5,215,713 | 6/1993 | Steinbiss | 422/61 |
| 5,217,874 | 6/1993 | Guadagno et al. | 435/28 |
| 5,264,181 | 11/1993 | Schreiber | 422/58 |
| 5,265,620 | 11/1993 | Fisher | 600/549 |
| 5,278,075 | 1/1994 | Stone | 436/73 |

*Primary Examiner*—Maureen M. Wallenhorst
*Attorney, Agent, or Firm*—Connors & Assoc.; John J. Connors

[57] ABSTRACT

A device 10 detects the presence of occult blood in feces by employing a sheet 12 of brittle material in which are formed a plurality of chambers 18 holding a liquid reagent solution juxtaposed to an absorbant material 14 impregnated with a guaiac material. The individual chambers 18 provide individual liquid tight enclosures that have thin walls that rupture to release the reagent solution when the device 10 is used to wipe feces from the rectum. The reagent solution reacts with the guaiac material to produce a blue color in the presence of occult blood in the feces.

17 Claims, 2 Drawing Sheets

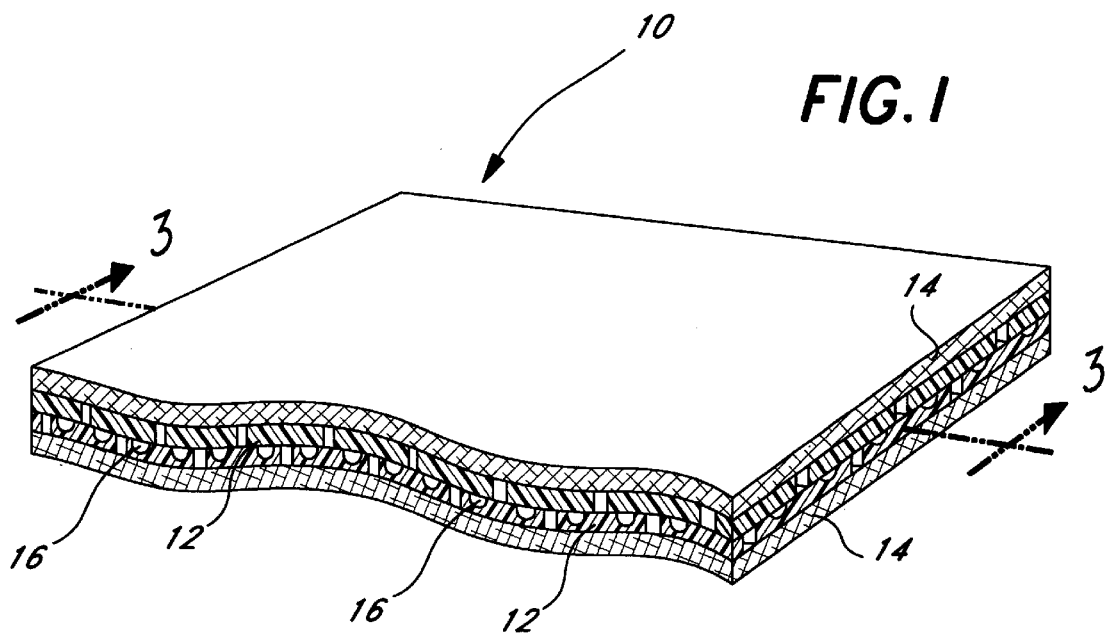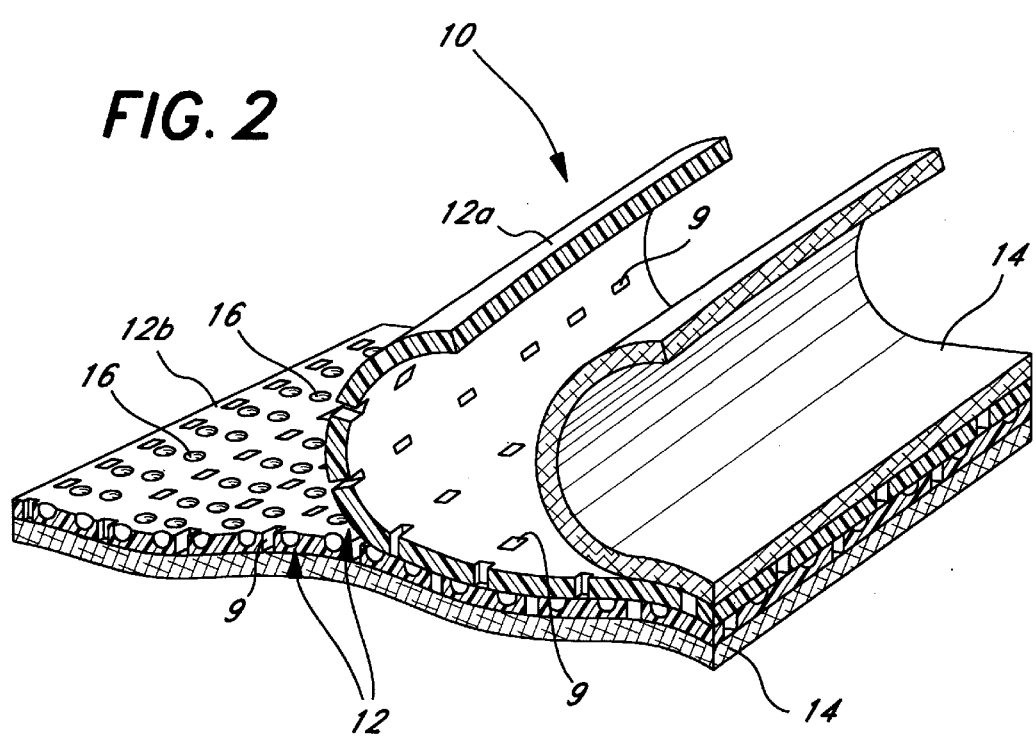

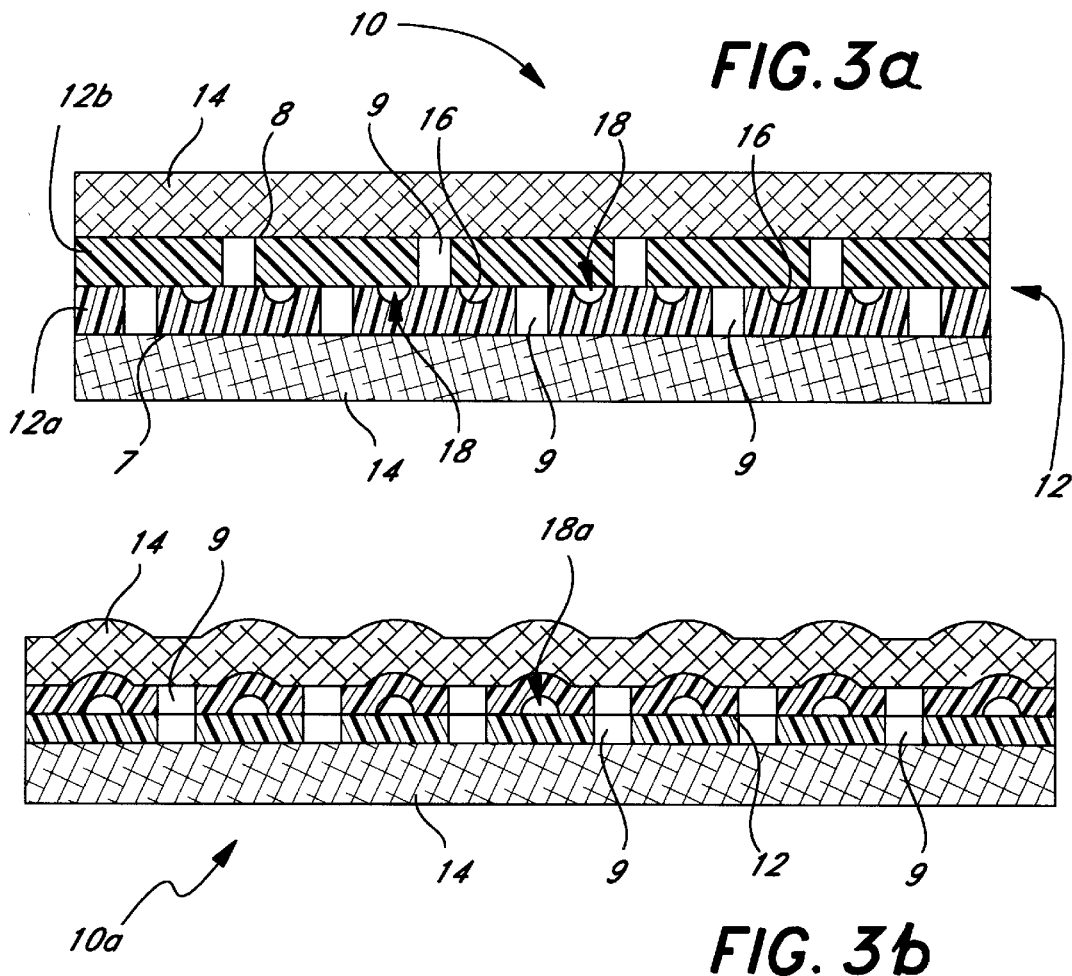
FIG. 3a
FIG. 3b
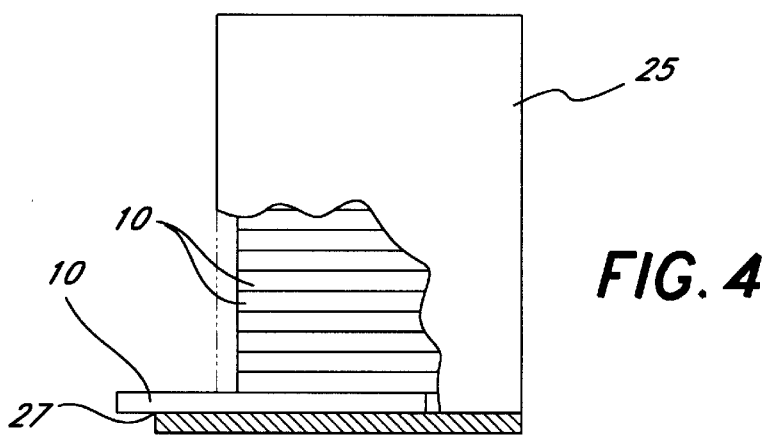
FIG. 4

BLOOD IN FECES TEST DEVICE

BACKGROUND OF THE INVENTION

1. Field of the Invention

This invention relates to a test device used to detect occult blood in feces, and particularly to a sheet of toilet paper like material that has test reagents separated, but released when the device is used to wipe feces from the anus of the person being tested.

2. Background Discussion

Occult blood in feces is an early sign of intestinal cancer or other disorders. It is undetectable to the naked eye, because the blood is present in minuet amounts. A well known test method employs guaiac resin material. This material reacts with a peroxide in the presents of occult blood to produce a blue color. A variety of guaiac materials maybe employed as well as various peroxide materials. Various test devices have been suggested, for example, U.S. Pat. Nos. 4,511,533 and 4,541,987 depict typical devices. None, however, have gained widespread acceptance because of the complexity of their structure.

SUMMARY OF THE INVENTION

It is the objective of this invention to provide a simple, sanitary and convenient way for an individual during the normal course of cleaning after defecation to test for occult blood using a toilet paper like device. The test device of this invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENTS," one will understand how the features of this invention provide its benefits, which include convenient and sanitary use and simplicity of manufacture.

The first feature of the test device of this invention is that it includes a sheet of brittle material in which are formed a plurality of chambers holding a liquid reagent solution. This sheet of brittle material is sandwiched between sheets of absorbant material impregnated with a guaiac material. The chambers holding the liquid reagent solution are juxtaposed to the absorbant material. The reagent solution is a mixture of a peroxide material and an alcohol, preferably the peroxide material is hydrogen peroxide or an organic peroxide, and preferably the alcohol is ethyl alcohol. Conventional reagent solutions are used in this invention.

The second feature of the test device of this invention is that the individual chambers provide individual liquid tight enclosures having thin walls that rupture to release the reagent solution when the device is used to wipe an anus. The sheet of brittle material forming the enclosures is made preferably from a polymeric material. Essentially any polymeric material may be used provided that it breaks easily. Specifically, the walls of the enclosures should break under normal pressure exerted by a person squeezing the assembly of sheets between his or her fingers, yet not be so fragile that simply a light tough breaks the chamber walls. Preferably, the breaking pressure should be 2.5 pounds per square inch or less. Typically, the breaking pressure will be from about 0.5 to 2.0 pounds per square inch. Typically, there are from 10 to 20 chambers per square inch of surface area of the sheet of brittle material. Each chamber normally has a capacity of from 0.25 to 0.5 milliliter.

Positioned adjacent and between the chambers are openings that extend between opposed sides of the sheet of brittle material. These openings permit the liquid reagent to flow from one side of the sheet of brittle material to the other side, so that the liquid contacts both sheets of absorbant material when the chambers are ruptured. The feces will be one one side of the device and the reagent solution wets the sheets of absorbant material. This is how the user detects that the chamber have been ruptured. If blood is present in the feces, the blue color appears on both sides of the device, because of the openings.

The third feature of the test device of this invention is that the sheets of absorbant material are paper, preferably, the paper is of a toilet paper quality. This paper is impregnated with guaiac material, which may be guaiac resin or an equivalent reactive substance.

This invention also includes a method for detecting occult blood in feces. This method includes the following steps:

(a) providing a device comprising a sheet of brittle material in which are formed a plurality of chambers holding a liquid reagent solution juxtaposed to a sheet of absorbant material impregnated with a guaiac material, and (b) using the device to wipe feces from an anus with enough force to rupture at least some of the chambers to release the reagent solution so that it reacts with the guaiac material to produce a blue color when there is occult blood in said feces.

The sheet of brittle material is sandwiched between a pair of sheets of absorbant material impregnated with a guaiac material, and each sheet of absorbant material is preferably paper of toilet paper quality.

DESCRIPTION OF THE DRAWING

The preferred embodiments of this invention, illustrating all its features, will now be discussed in detail. These embodiments depict the novel and non-obvious test device and method of this invention as shown in the accompanying drawing, which is for illustrative purposes only. This drawing includes the following figures (Figs.), with like numerals indicating like parts:

FIG. 1 is a perspective view of the test device of this invention,

FIG. 2 is a perspective view with some of the sheet materials forming the device peeled partially away.

FIG. 3A is a cross sectional view taken along line 3—3 of FIG. 1.

FIG. 3B is a cross sectional view of an alternate embodiment of this invention.

FIG. 4 is a side elevational view of a dispenser for the test device of this invention.

DETAILED DESCRIPTION OF THE PREFERRED EMBODIMENTS

As shown in FIG. 1 through FIG. 3, the test device 10 of this invention includes a multi-layered sheet 12 of polymeric material sandwich between two sheets of absorbent material 14, preferably paper of a toilet paper quality. The absorbent material 14 may comprise one or more plies of paper. This absorbent material 14 is impregnated with a guaiac material. A conventional technique is used for impregnating the absorbent material with the guaiac material is discussed subsequently.

The multi-layered polymeric material 12 comprises two layers 12a and 12b. One layer 12b has a plurality of indentations 16 therein. These indentations 16, when the second layer 12b is placed over the first layer 12a, form chambers 18 (FIG. 3) which enclose a liquid reagent, preferably comprised in a mixture of ethyl alcohol and hydrogen peroxide. This polymeric intermediate sheet 12 is formed by placing the one layer 12b on a flat surface and filling the indentations 16 with the liquid. The second layer 12a is placed over the first layer 12b and a combination of heat and mild pressure is applied to the assembly of layers, so that they are bonded together forming a plurality of liquid tight chambers 18 holding the reagent solution of peroxide and alcohol. This multi-layered polymeric material 12 is then sandwiched between the two sheets of the absorbent material 14. Care must be taken so that only very light pressure is applied when assembling the sheets of absorbent material 14 and the polymeric sheet 12 so that the chambers 18 do not break. As shown in FIG. 3B, an alternate embodiment device 10a uses the chambers 18a as raised bubbles. These are easy for the user to feel when using the device 10a.

In accordance with one feature of this invention, there are positioned adjacent and between the chambers 18 openings 9 that extend between opposed sides of the sheet of polymeric material 12. These openings 9 permit the liquid reagent to flow from one side 7 of the sheet of brittle material to the other side 8, so that the liquid contacts both sheets of absorbant material 14 when the chambers are ruptured.

As shown in FIG. 4, the devices 10 may be in the form of a individual sheets about three inches square that are stacked upon each other in a case 25 with an open mouth 27 from which the individual sheets are withdrawn. Since the polymeric sheet 12 contains a multitude of very easily ruptured chambers 18, only a light pressure will result in several of the chambers 18 fracturing to release the reagent solution when pressure is applied during use. This breaking pressure is less than 2.5 pounds per square inch. The device 10 may be handled, but when pressure is applied when wiping feces from the anus, there is sufficient breaking pressure to fracture the chambers 18 and release of the reagent solution. Thus, there is provided a convenient device and method for testing the presence of cult blood in feces.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

I claim:

1. A device for detecting the presence of occult blood in feces, comprising a sheet of brittle material in which are formed a plurality of chambers holding a liquid reagent solution, said sheet of brittle material being sandwiched between sheets of absorbant material, at least one of said sheets of absorbant material being impregnated with a guaiac material, said plurality of chambers providing individual liquid tight enclosures having thin walls that rupture to release the reagent solution when the device is used to wipe feces from an anus, said released liquid reagent solution reacting with the guaiac material in the presence of occult blood in feces to produce a color that so indicates the presence of occult blood in the feces collected by wiping the anus.

2. The device of claim 1 where there are positioned adjacent and between the chambers openings that extend between opposed sides of the sheet of brittle material, said openings permitting the liquid reagent solution to flow from one side of the sheet of brittle material to the other side, so that the liquid contacts both sheets of absorbant material when the chambers are ruptured.

3. The device of claim 1 where the walls of the chambers break under normal pressure exerted by a person squeezing the device between his or her fingers, yet not being so fragile that a light touch breaks the chambers.

4. The device of claim 1 where the chambers rupture at an applied pressure of 2.5 pounds per square inch or less.

5. The device of claim 1 where the pressure at which the chambers rupture ranges from 0.5 to 2.0 pounds per square inch.

6. The device of claim 1 where the reagent solution is a mixture of a peroxide material and an alcohol.

7. The device of claim 1 where the sheet of brittle material forming the chambers is made from a polymeric material.

8. The device of claim 1 where there are from 10 to 20 chambers per square inch of surface area of the sheet of brittle material.

9. The device of claim 1 where the chambers have a capacity of from 0.25 to 0.5 milliliter.

10. The device of claim 1 where the sheets of absorbant material are paper.

11. The device of claim 10 where the paper is of toilet paper quality.

12. A device for detecting the presence of occult blood in feces, comprising a sheet of brittle material in which are formed a plurality of chambers holding a liquid reagent solution, said sheet of brittle material being juxtaposed to an absorbant material impregnated with a guaiac material, said plurality of chambers providing individual liquid tight enclosures having thin walls that rupture to release the reagent solution when the device is used to wipe feces from an anus, said walls rupturing at a pressure of 2.5 pounds per square inch or less, and wherein there are positioned adjacent and between the chambers, openings that extend between opposed sides of the sheet of brittle material, said openings permitting the liquid reagent solution to flow from one side of the sheet of brittle material to the other side, to insure that the liquid contacts the absorbant material when the chambers are ruptured, said reagent solution reacting with the guaiac material to produce a blue color in the presence of occult blood in feces.

13. A method for detecting occult blood in feces, comprising (a) providing a device comprising a sheet of brittle material in which are formed a plurality of chambers holding a liquid reagent solution, said sheet of brittle material being juxtaposed to a sheet of absorbant material impregnated with a guaiac material, and (b) using the device to wipe feces from an anus with enough force to rupture at least some of the chambers to release the reagent solution so that it reacts with the guaiac material to produce a blue color when there is occult blood in said feces.

14. The method of claim 13 where the sheet of brittle material is sandwiched between a pair of sheets of absorbant material, at least one of said sheets of absorbant material being impregnated with a guaiac material.

15. The method of claim 14 where there are positioned adjacent and between the chambers openings that extend between opposed sides of the sheet of brittle material, said openings permitting the liquid reagent solution to flow from one side of the sheet of brittle material to the other side, so that the liquid contacts both sheets of absorbant material when the chambers are ruptured.

16. The method of claim 13 where the chambers rupture at a pressure of 2.5 pounds per square inch or less.

17. The method of claim 13 where the force to rupture at least some of the chambers ranges from 0.5 to 2.0 pounds per square inch.

* * * * *